(12) United States Patent
Barry et al.

(10) Patent No.: US 8,944,318 B2
(45) Date of Patent: Feb. 3, 2015

(54) WORKFLOW MANAGEMENT SYSTEM

(71) Applicant: Elekta AB, Stockholm (SE)

(72) Inventors: Paul Barry, South Yorkshire (GB); Peter Carey, London (GB); Tim Prosser, Lawrenceville, GA (US)

(73) Assignee: Elekta AB, Stockholm (SE)

( * ) Notice: Subject to any disclaimer, the term of this patent is extended or adjusted under 35 U.S.C. 154(b) by 95 days.

(21) Appl. No.: 13/628,825

(22) Filed: Sep. 27, 2012

(65) Prior Publication Data

US 2014/0084058 A1  Mar. 27, 2014

(51) Int. Cl.
| | | |
|---|---|---|
| G06F 19/00 | (2011.01) | |
| G06Q 50/22 | (2012.01) | |
| A61N 5/10 | (2006.01) | |
| G06K 7/10 | (2006.01) | |

(52) U.S. Cl.
CPC ............. G06Q 50/22 (2013.01); A61N 5/1049 (2013.01); G06F 19/3481 (2013.01); G06K 7/10009 (2013.01)
USPC ......................................... 235/380; 235/385

(58) Field of Classification Search
CPC .. G06Q 10/06; G06Q 10/08; G06Q 10/06311
USPC ................ 235/380, 385, 462.46, 472.02
See application file for complete search history.

(56) References Cited

U.S. PATENT DOCUMENTS

| | | | |
|---|---|---|---|
| 8,275,442 B2* | 9/2012 | Allison | 600/407 |
| 2008/0031414 A1* | 2/2008 | Coppens | 378/65 |
| 2008/0071420 A1* | 3/2008 | Guertin et al. | 700/228 |
| 2009/0102612 A1 | 4/2009 | Dalbow et al. | |
| 2010/0067660 A1* | 3/2010 | Maurer et al. | 378/95 |

FOREIGN PATENT DOCUMENTS

| | | |
|---|---|---|
| EP | 1697004 | 9/2006 |
| WO | WO 2005/044378 | 5/2005 |

OTHER PUBLICATIONS

Sanden; "Experience the Elekta Difference"; Elekta European Users Meeting at ESTRO; May 7, 2011; 2 pages; Elekta AB.

* cited by examiner

*Primary Examiner* — Danie St Cyr
(74) *Attorney, Agent, or Firm* — Sean D. Detweiler, Esq.; Morse, Barnes-Brown & Pendleton, P.C.

(57) ABSTRACT

A workflow management system for radiotherapy treatment of a patient using radiotherapy equipment comprising: a patient radiofrequency identification (RFID) tag and a radiofrequency (RF) detection device, which provides a patient unique identifier matchable to a patient's treatment plan; a plurality of optical markers, wherein in at least one patient optical marker is positioned on the patient and at least one reference optical marker is positioned at a reference point on the radiotherapy equipment; an optical reader to detect each of the plurality of optical markers; wherein the system matches the patient's unique identifier to the patient treatment plan.

17 Claims, 2 Drawing Sheets

WORKFLOW MANAGEMENT SYSTEM

FIELD OF THE TECHNOLOGY

The present technology relates to a workflow management system used with radiotherapy treatment (also known as radiation therapy or radiation oncology), including the planning/simulation stages of patient treatment prior to the delivery of radiation.

BACKGROUND OF THE TECHNOLOGY

The accurate delivery of radiotherapy treatment relies on the clinical staff to ensure that a patient is correctly identified prior to treatment and that the treatment plan and equipment used are also correct. Safety checks are in place to minimize the risk of errors and current clinical practice makes use of the expertise of clinical staff to safely carry out radiotherapy treatment.

However, radiotherapists and other clinical staff work under severe time constraints. The "invisible" and complex nature of the radiotherapy treatment means that patients are often unable to understand and be confident in the accuracy of their treatment. There exists a need for a "double-check" in addition to the expertise of the clinical staff to re-assure patients and "back-up" the safety procedures carried out by radiotherapists.

Furthermore, a significant proportion of the time taken to treat patients in today's busy radiotherapy departments is the time taken to set-up the patient and the necessary equipment accessories. Any reduction in the set-up time will increase the patient throughput i.e. the number of patients that can be treated in any given day.

SUMMARY

The present technology sets out to provide an improved workflow management system which alleviates the problems described above by increasing safety and patient confidence.

In one aspect, the technology provides a workflow management system for radiotherapy treatment of a patient using radiotherapy equipment comprising:

a patient radiofrequency identification (RFID) tag and a radiofrequency (RF) detection device, which provides a unique identifier matchable to a patient's treatment plan;

a plurality of optical markers, wherein in at least one patient optical marker is positioned on the patient and at least one reference optical marker is positioned at a reference point on the radiotherapy equipment;

an optical reader to detect each of the plurality of optical markers;

wherein the system matches the patient's unique identifier to the patient treatment plan.

The workflow management system of one embodiment of the technology safely integrates tagging equipment into the treatment process, without interfering with existing clinical practice. The workflow management system of one embodiment of the technology eliminates the risk that the wrong patient will be treated due to inaccurate identification or that the wrong treatment plan or treatment location will be used. The workflow management system achieves this improvement in safety without adding to the time pressures placed on clinical staff, by streamlining the treatment workflow with minimal user interaction to maximize patient throughput. RFID technology is used to ensure that each patient can be uniquely identified, whilst the form of the RFID tag can be designed to achieve patient comfort. The optical marker/reader combination has been found to provide accurate line-of-sight detection of the patient position. The present technology provides an independent automatic verification of patient identity and ensures that the correct treatment plan and treatment location is used for each treatment during a course of radiotherapy.

Preferably, the workflow management system further comprises a display to display confirmation that the patient's unique identifier is matched to the patient treatment plan.

A display is provided to act as a "double-check" to reassure both the clinical staff and the patient that treatment is safe.

Preferably, the patient radiofrequency identification (RFID) tag is in the form of a small sticker; a plaster; a dressing; a bracelet or in the style of a watch.

The radiofrequency identification tag (RFID) tag is designed to take into account the diverse nature of patients that undergo radiotherapy treatment. Radiotherapy treatment can take several weeks and the design is selected to be suitable for a patient to wear for the full length of the treatment, i.e. from treatment simulation to completion of radiotherapy, without the wearer being identified as a cancer patient. It is envisaged that a range of RFID tags may be offered to the patient for them to select a style that they are most comfortable with, but which is also suited to the size of the patient, for example for pediatric patients.

Preferably, the patient optical marker is placed below the treatment isocentre.

More preferably, the patient optical marker is placed at a distance of between about 100 mm and about 200 mm from the treatment isocentre.

The patient optical marker is positioned according to the radiotherapist's understanding of the treatment plan. It is envisaged that the patient optical marker will be positioned as close as possible to the treatment isocentre so that the movement of the patient optical marker relates as closely as possible to the movement of the treatment isocentre, i.e. the treatment target. However, the patient optical marker should be positioned at a sufficient distance from the treatment isocentre to stay out of the treatment beam. The distance of the beam from the isocentre will depend on the anatomical position of the target and the need for the patient optical marker to be in the line-of-sight of the optical reader.

Preferably, the workflow management system comprises two reference optical markers placed on opposing sides of the upper face of a patient support.

The number and position of the reference optical markers can be selected according to the treatment plan and the selected position of the patient optical marker. The use of two or more reference optical markers ensures accurate localization and subsequent monitoring of the patient optical marker. The "upper face" of the patient support is understood to be the face of the patient support on which the patient is supported.

Preferably, the workflow management system comprises at least one accessory optical marker positioned on or within a radiotherapy equipment accessory, which is detectable by the optical reader.

More preferably, the workflow management system matches the patient unique identifier to the or each detected accessory optical marker.

Preferably, the optical reader has a positional accuracy of about 4 mm.

The optical reader is able to detect and monitor the position of the or each optical marker within an accuracy of about 4 mm. The optical reader is used to detect "gross" movements of the patient, i.e. of around 10 mm or more. Although the workflow management system is not used for monitoring the movement of the isocentre, the system is able to locate the position of the or each optical marker to within a high degree of accuracy.

More preferably, the display means is configured to display confirmation that the patient unique identifier is matched to the or each detected accessory optical marker.

Preferably, the display means is configured to display a color-coded message.

Preferably, the workflow management system reports the position of the patient optical marker.

In a second aspect, the present technology provides a workflow management method comprising the steps of:

detecting a patient unique identifier from a patient radiofrequency identification (RFID) tag;

monitoring a plurality of optical markers, wherein in at least one patient optical marker is positioned on the patient and at least one reference optical marker is positioned at a reference point on the radiotherapy equipment;

matching the patient unique identifier to the patient treatment plan and the monitored equipment accessories.

Preferably, the workflow management method further comprises the step of displaying confirmation that the patient unique identifier is matched to the patient treatment plan and the equipment accessories.

Preferably, the workflow management method further comprises the step of monitoring at least one accessory optical marker positioned on or within an equipment accessory, for use in treatment.

Preferably, the workflow management method further comprises the step of storing the position of the patient optical marker and/or the at least one accessory optical marker.

Storing the position of the or each optical marker allows for uniformity across each treatment of a course of radiotherapy.

More preferably, the workflow management method further comprises the step of selecting a tolerated range of movement through which the patient optical marker is permitted to move.

Preferably, the workflow management method further comprises the step of interrupting treatment if the movement of the patient optical marker is detected to have moved outside the selected tolerated range of movement By selecting a tolerance of permitted movement, the system will allow treatment to continue during "normal" patient movement, e.g. breathing, but will stop treatment if the patient were to fall off or dismount the treatment table. This is an important safety feature, which allows for treatment to stop immediately without relying on the reactions of a radiotherapist.

Preferably, the workflow management method further comprises the step of reporting the position of the patient optical marker.

The position of the patient optical marker can be recorded to allow the same marker position to be used for each subsequent treatment during a course of radiotherapy.

In a third aspect the technology provides a computer-readable carrier medium carrying computer readable instructions for performing the workflow management method of the present technology.

For the purposes of clarity and a concise description, features are described herein as part of the same or separate embodiments; however it will be appreciated that the scope of the technology may include embodiments having combinations of all or some of the features described.

BRIEF DESCRIPTION OF THE FIGURES

These and other characteristics of the present technology will be more fully understood by reference to the following detailed description in conjunction with the attached drawings, in which.

DETAILED DESCRIPTION

Figure 1:
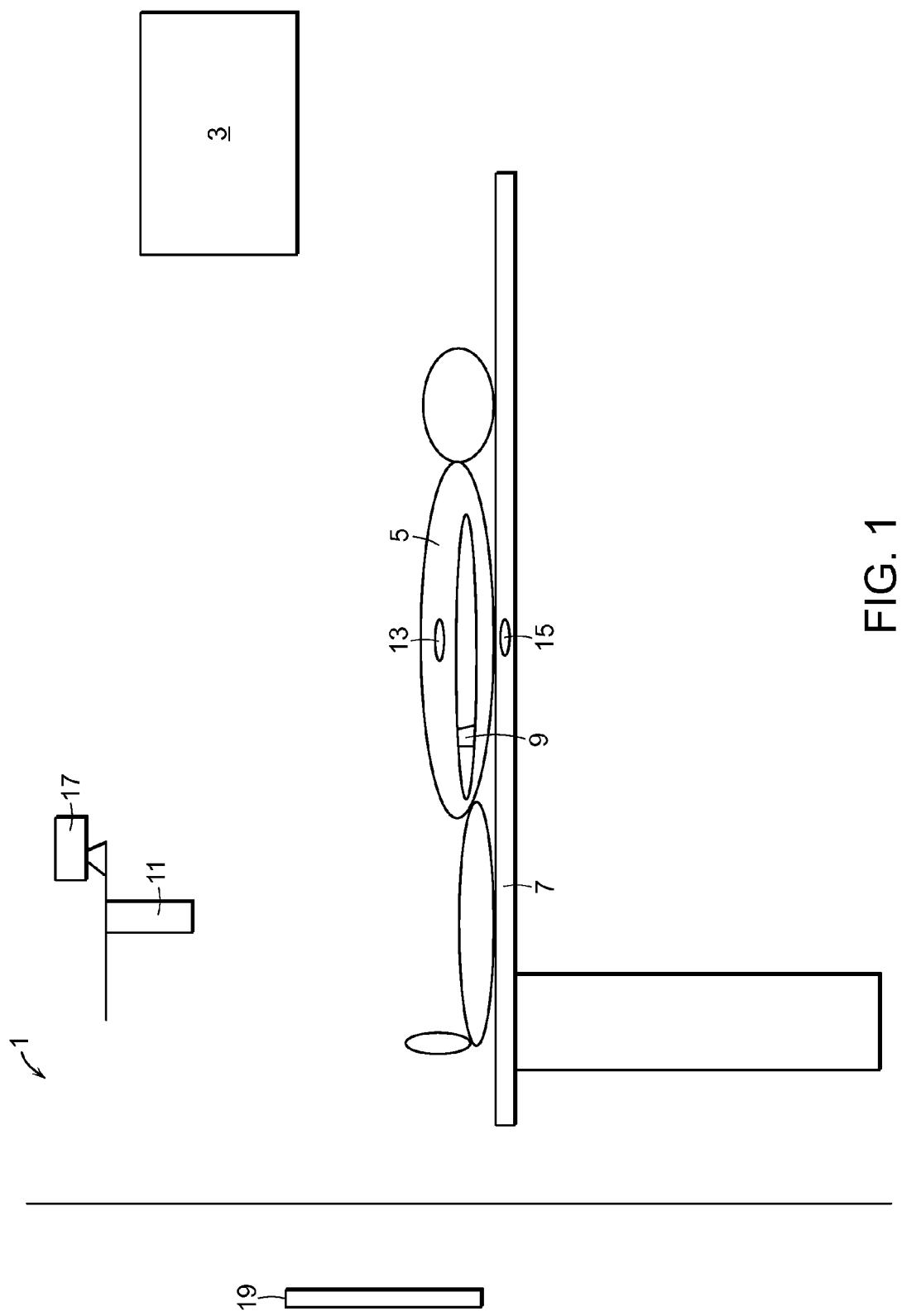
FIG. 1 is a schematic view of the workflow management system in accordance with an example embodiment of the present technology.
Figure 2:
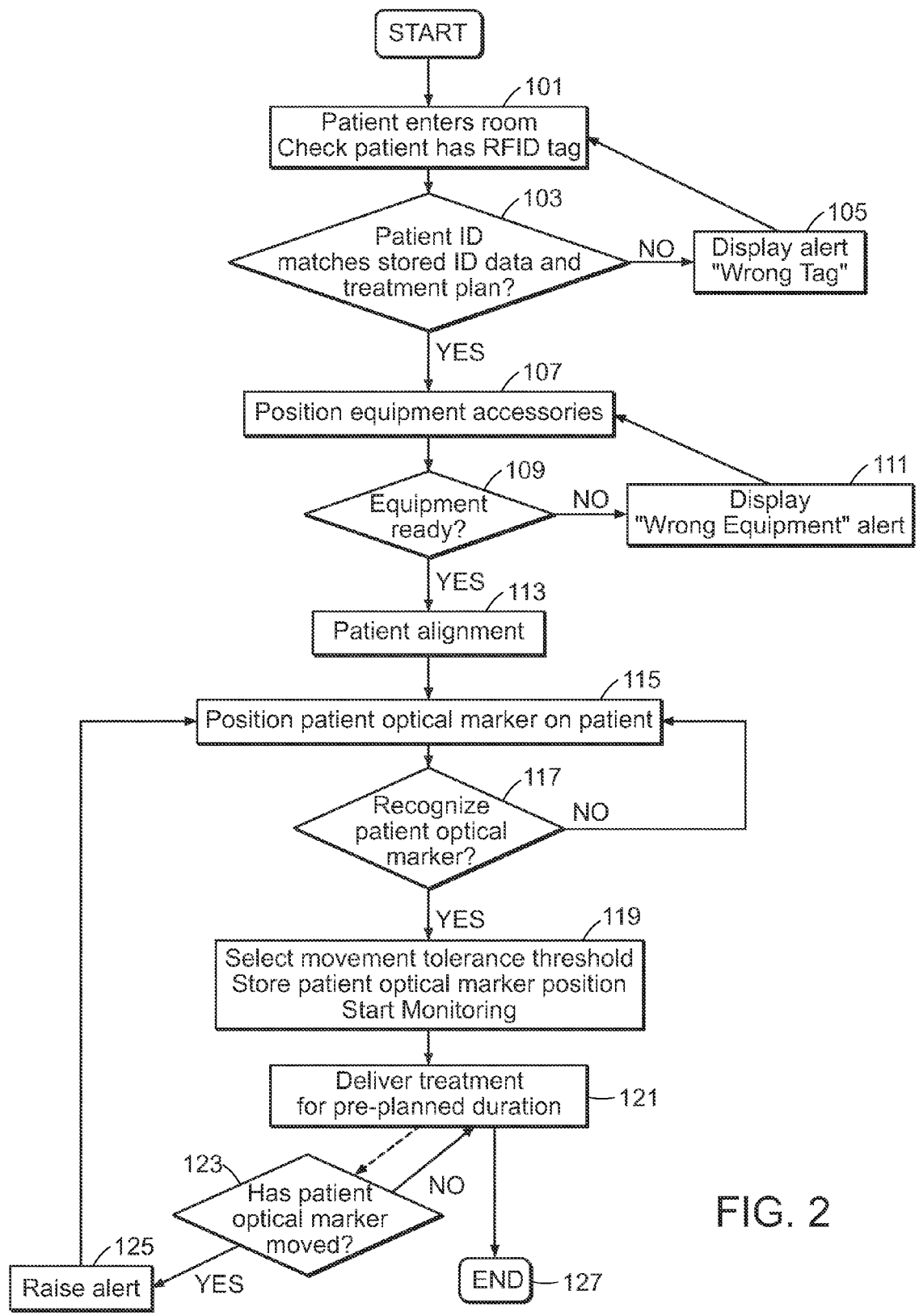
FIG. 2 is a flow diagram of a workflow management method in accordance with an example embodiment of the present technology.

FIGS. 1 and 2, wherein like parts are designated by like reference numerals throughout, illustrate example embodiments of a workflow management system and method according to the present technology. Although the present technology will be described with reference to the example embodiments illustrated in the figures, it should be understood that many alternative forms can embody the present technology. One of skill in the art will additionally appreciate different ways to alter the parameters of the embodiments disclosed, such as the size, shape, or type of elements or materials, in a manner still in keeping with the spirit and scope of the present technology.

Referring to FIG. 1, an example embodiment of a workflow management system is depicted. In the example embodiment of FIG. 1, the workflow management system 1 of the present technology is shown with radiotherapy apparatus 3 in a set-up position. A patient 5 is lying on a patient support 7. The patient 5 is wearing a radiofrequency identification tag (RFID tag) 9 in the form of a bracelet. The RFID tag can be embedded or encased in a protective plastic casing. It is envisaged that the RFID tag is disposable so that the ID is unique to a patient. However the protective casing in the form of a bracelet, watch etc. may be re-usable. A radiofrequency (RF) reader array 11 is positioned above the patient support 7.

A patient optical marker 13 is placed below the treatment isocentre and is used to confirm that the patient 5 is on the patient support 7. In the embodiment shown in FIG. 1 the patient optical marker 13 is placed on the torso of the patient 5. A first reference optical marker 15 is placed or fixed to one side of the upper face of the patient support 7. A second reference optical marker (not shown) is placed or fixed on the opposing side of the upper face of the patient support 7.

An optical reader 17, for example a Polaris camera with a positional accuracy of about 4 mm, is positioned on the radiotherapy apparatus 3 or mounted at any desired position within the treatment room to allow for a maximum view of the optical markers 13, 15. The optical reader detects gross movements of the patient. Although the optical reader is not used for tracking motion of the treatment isocentre, it can detect any patient movement greater than about 10 mm. For example, if the patient 5 were to fall off the patient support 7 or stand up from the patient support 7, this would displace the patient optical marker 13 more than 10 mm and the workflow management system 1 would be alerted. Similarly, if the patient RFID tag 9 or patient optical marker 13 falls off or is removed, the system 1 would be alerted. Any movement of the patient greater than 10 mm will alert the system. If an alert is generated a hazard notice is displayed outside of the treatment room on a display 19. The display 19 is a computer screen of a hand-held wireless device such as a mobile telephone, a "smart" phone, a tablet, or a computer screen of a laptop PC, a netbook PC or, in an alternative embodiment is a wall-mounted computer screen of a desktop PC.

In the example of FIG. 1, the patient optical marker 15 does not mark any clinically relevant position e.g. the target isocentre. The position of the target isocentre will be monitored according to established procedure, referred to below, wherein tattoos on the patient's body are aligned with laser beams in the treatment room. In the embodiment shown in FIG. 1 and the workflow method of FIG. 2 any motion monitoring during treatment, beyond the "gross" movement referred to, for example detection of the patient leaving the patient support, is entirely optional. It is understood that the optical markers (and the RFID tag) are positioned outside of the treatment field. It is preferred that the patient optical tag 15 is placed below the isocentre, but this will depend on the position of the target. Depending on the treatment plan, it may be necessary to place the patient optical marker 15 a significant distance away from the treatment isocentre.

If the radiotherapy treatment requires equipment accessories to be used, each accessory also has an accessory optical marker positioned within or on the accessory, such that the marker is readable by the optical reader 17. Equipment accessories include, but are not limited to, patient positioning/immobilization devices and beam-shaping devices. The optical reader/camera 17 is carefully positioned so that all the patient, reference and accessory optical markers 13, 15 are all within the camera's field of view.

Referring to FIG. 2 depicting an example of the workflow management method of the present technology, at step 101 a patient enters the treatment room with their previously allocated RFID tag. The RFID tag is tracked prior to treatment, i.e. during treatment simulation. The unique identifier stored on the RFID tag is detected by the RF reader. At step 103, the RFID is then matched to identification data stored within the treatment plan of the oncology information system, such as Elekta's MOSAIQ treatment planning system. The system matches the patient RFID to the patient records, including medical records and treatment plan. If the RFID matches the oncology information system's ID data then a confirmation message is displayed, for example using color coding with a green dot to indicate a positive match. At step 105, if the RFID does not match the treatment planning ID data then a "Wrong Tag" alert is displayed, for example with a red dot to indicate that the RFID tag and planning data need to be checked again.

After matching patient RFID to the treatment plan ID, at step 107, the equipment accessories are gathered and placed in position. Each accessory has an integral optical marker. For example, the optical marker is built into the equipment accessory. In alternative embodiments, the optical marker is retrofitted to the equipment accessory. At step 109, each optical marker is detected by the optical reader and the system checks that the equipment is ready and in the correct position. If the equipment is correct then the system proceeds. At step 111, if a piece of equipment is missing or incorrectly positioned then a "Wrong Equipment" alert is displayed with a red dot to indicate that the optical markers and equipment accessories needs to be checked again.

In an alternative embodiment of the present technology, it is envisaged that the equipment accessories could be marked with RFID tags. This will not provide the system with any positional information, but will improve the set-up process by confirming the presence of the correct equipment accessories. Such an RFID tagging system will correlate the correct patient and equipment accessories and will inform the clinical staff if there are any errors. However, the correct position of the equipment accessories will need to be checked manually. In further embodiments of the present technology, it is envisaged that a combination of RF and optical markers could be used to adapt the system and method to a user's requirements.

With patient identity verified and the correct equipment accessories in place, an established procedure for patient alignment is carried out at step 113. For example, tattoos on the patient's body are aligned with laser beams in the treatment room.

With the patient ID and accessories verified and the patient aligned in the treatment position, at step 115 a patient optical marker is placed on the patient. At step 117, the system asks whether the optical reader recognizes, i.e. detects the patient optical marker. To allow the system to recognize the patient optical marker, detection of the equipment accessory optical markers is effectively put on hold. When the patient optical marker is positioned on the patient and introduced to the workflow management system, it is recognized that the "new" marker is the patient optical marker. If the patient optical marker is not recognized then it is re-positioned and re-checked. If the marker is recognized then, at step 119, the position of the marker is calculated with reference to the two reference optical markers on either side of the patient support. The position of the patient optical marker is stored and a tolerance of movement is selected.

At step 121, treatment begins and is carried out according to the treatment plan. At step 123, the system continually monitors the real-time position of the patient optical marker, and the equipment accessory optical markers if used, during the pre-planned duration of the treatment and raises an alert, at step 125, if any problems occur. If, during treatment, the patient optical marker is detected to have moved beyond the tolerated range of movement, the system will raise an alert status and stop the treatment. For example, an "interlock raised alarm" status causes the radiotherapy apparatus to automatically shut down. The tolerance of movement selected at step 119 will allow treatment to continue during "normal" patient movement, e.g. breathing, but will stop treatment if the patient were to fall off or dismount the treatment table. If no alerts are raised and the optical marker does not move beyond the tolerated range of movement, the treatment continues until completed at step 127. It is also understood that if patient ID or the equipment accessories are incorrect at any stage prior to the start of the treatment, then the workflow management system will not allow treatment to commence.

Any values and dimensions provided herein are illustrative and in no way limiting of the present technology. Upon reading the present specification, one of skill in the art will appreciate a wide variety of other depths, dimensions, and the like that can be used to implement the workflow management system and method. All such alternatives and modifications are contemplated within the scope of the present technology.

The above described embodiment has been given by way of example only, and the skilled reader will naturally appreciate that many variations could be made thereto without departing from the scope of the claims.

Numerous modifications and alternative embodiments of the present technology will be apparent to those skilled in the art in view of the foregoing description. Accordingly, this description is to be construed as illustrative only and is for the purpose of teaching those skilled in the art the best mode for carrying out the present technology. Details of the technology may vary substantially without departing from the spirit of the present technology, and exclusive use of all modifications that come within the scope of the appended claims is reserved. It is intended that the present technology be limited only to the extent required by the appended claims and the applicable rules of law.

It is also to be understood that the following claims are to cover all generic and specific features of the technology described herein, and all statements of the scope of the technology which, as a matter of language, might be said to fall therebetween.

The above-described examples of workflow management, and corresponding method and system can be implemented in digital electronic circuitry, in computer hardware, firmware, and/or software. The implementation can be as a computer program product. The implementation can, for example, be in a machine-readable storage device, for execution by, or to control the operation of, data processing apparatus. The implementation can, for example, be a programmable processor, a computer, and/or multiple computers. The implementation can, for example, a computer-readable carrier medium carrying computer readable instructions.

A computer program can be written in any form of programming language, including compiled and/or interpreted languages, and the computer program can be deployed in any form, including as a stand-alone program or as a subroutine, element, and/or other unit suitable for use in a computing environment. A computer program can be deployed to be executed on one computer or on multiple computers at one site.

Method steps can be performed by one or more programmable processors executing a computer program to perform functions of the technology by operating on input data and generating output. Method steps can also be performed by and an apparatus can be implemented as special purpose logic circuitry. The circuitry can, for example, be a FPGA (field programmable gate array) and/or an ASIC (application-specific integrated circuit). Subroutines and software agents can refer to portions of the computer program, the processor, the special circuitry, software, and/or hardware that implement that functionality.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer can be operatively coupled to receive data from and/or transfer data to one or more mass storage devices for storing data (e.g., magnetic, magneto-optical disks, or optical disks).

Data transmission and instructions can also occur over a communications network. Computer program products suitable for embodying computer program instructions and data include all forms of non-volatile memory, including by way of example semiconductor memory devices. The computer program products can, for example, be EPROM, EEPROM, flash memory devices, magnetic disks, internal hard disks, removable disks, magneto-optical disks, CD-ROM, and/or DVD-ROM disks. The processor and the memory can be supplemented by, and/or incorporated in special purpose logic circuitry.

To provide for interaction with a user, the above described techniques can be implemented on a computer having a display device. The display device can, for example, be a cathode ray tube (CRT) and/or a liquid crystal display (LCD) monitor. The interaction with a user can, for example, be a display of information to the user and a keyboard and a pointing device (e.g., a mouse or a trackball) by which the user can provide input to the computer (e.g., interact with a user interface element). Other kinds of devices can be used to provide for interaction with a user. Other devices can, for example, be feedback provided to the user in any form of sensory feedback (e.g., visual feedback, auditory feedback, or tactile feedback). Input from the user can, for example, be received in any form, including acoustic, speech, and/or tactile input.

The above described techniques can be implemented in a distributed computing system that includes a back-end component. The back-end component can, for example, be a data server, a middleware component, and/or an application server. The above described techniques can be implemented in a distributing computing system that includes a front-end component. The front-end component can, for example, be a client computer having a graphical user interface, a Web browser through which a user can interact with an example implementation, and/or other graphical user interfaces for a transmitting device. The components of the system can be interconnected by any form or medium of digital data communication (e.g., a communication network). Examples of communication networks include a local area network (LAN), a wide area network (WAN), the Internet, wired networks, and/or wireless networks.

The system can include clients and servers. A client and a server are generally remote from each other and typically interact through a communication network. The relationship of client and server arises by virtue of computer programs running on the respective computers and having a client-server relationship to each other.

Packet-based networks can include, for example, the Internet, a carrier internet protocol (IP) network (e.g., local area network (LAN), wide area network (WAN), campus area network (CAN), metropolitan area network (MAN), home area network (HAN)), a private IP network, an IP private branch exchange (IPBX), a wireless network (e.g., radio access network (RAN), 802.11 network, 802.16 network, general packet radio service (GPRS) network, HiperLAN), and/or other packet-based networks. Circuit-based networks can include, for example, the public switched telephone network (PSTN), a private branch exchange (PBX), a wireless network (e.g., RAN, bluetooth, code-division multiple access (CDMA) network, time division multiple access (TDMA) network, global system for mobile communications (GSM) network), and/or other circuit-based networks.

The transmitting device can include, for example, a computer, a computer with a browser device, a telephone, an IP phone, a mobile device (e.g., cellular phone, personal digital assistant (PDA) device, laptop computer, electronic mail device), and/or other communication devices. The browser device includes, for example, a computer (e.g., desktop computer, laptop computer) with a world wide web browser (e.g., Microsoft® Internet Explorer® available from Microsoft Corporation, Mozilla® Firefox available from Mozilla Corporation). The mobile computing device includes, for example, a Blackberry®.

Comprise, include, and/or plural forms of each are open ended and include the listed parts and can include additional parts that are not listed. And/or is open ended and includes one or more of the listed parts and combinations of the listed parts.

What is claimed is:

1. A workflow management safety system for radiotherapy treatment of a patient using radiotherapy equipment comprising:
    a patient radiofrequency identification (RFID) tag and a radiofrequency (RF) detection device, which provides a patient unique identifier matchable to a patient's treatment plan;
    a plurality of optical markers, the plurality of markers including at least one patient optical marker;
    at least one reference optical marker positioned at a reference point on or within the radiotherapy equipment;
    at least one accessory optical marker positioned on or within a radiotherapy equipment accessory; and
    an optical reader to detect each of the plurality of optical markers;

wherein the system matches the patient's unique identifier to the patient treatment plan and to at least one of the detected patient optical marker and the at least one accessory optical marker.

2. The workflow management safety system according to claim 1 further comprising a display to display confirmation that the patient's unique identifier is matched to the patient treatment plan.

3. The workflow management safety system according to claim 2 wherein the display is configured to display confirmation that the patient unique identifier is matched to the or each detected accessory optical marker.

4. A workflow management system according to claim 2 wherein the display is configured to display a color-coded message.

5. The workflow management safety system according to claim 1 wherein the patient radiofrequency identification (RFID) tag is in the form of a small sticker; a plaster; a dressing; a bracelet or in the style of a watch.

6. The workflow management safety system according to claim 1 wherein the patient optical marker is placed below the treatment isocentre.

7. The workflow management safety system according to claim 1 wherein the patient optical marker is placed at a distance of between about 100 mm and about 200 mm from the treatment isocentre.

8. The workflow management safety system according to claim 1 wherein the workflow management system comprises two reference optical markers placed on opposing sides of the upper face of a patient support.

9. The workflow management safety system according to claim 1 wherein the workflow management system reports the position of the patient optical marker.

10. A workflow safety management method comprising the steps of:
  detecting a patient unique identifier from a patient radiofrequency identification (RFID) tag;
  monitoring a plurality of optical markers, wherein in at least one patient optical marker is positioned on the patient and at least one reference optical marker is positioned at a reference point on the radiotherapy equipment;
  monitoring at least one accessory optical marker positioned on or within a radiotherapy equipment accessory;
  matching the patient unique identifier to the patient treatment plan and to the at least one accessory optical marker.

11. The workflow management safety method according to claim 10 wherein at least one of: i) the position of the at least one patient optical marker and ii) the at least one reference optical marker is monitored with a positional accuracy of greater than or equal to 4 mm.

12. The workflow management safety method according to claim 10 further comprising the step of displaying confirmation that the patient unique identifier is matched to the patient treatment plan and/or the or each radiotherapy equipment accessory.

13. The workflow management safety method according to claim 10 further comprising the step of storing the position of the patient optical marker and/or the at least one accessory optical marker.

14. The workflow management safety method according to claim 10 further comprising the step of selecting a tolerated range of movement through which the patient optical marker is permitted to move.

15. The workflow management safety method according to claim 14 further comprising the step of interrupting treatment if the movement of the patient optical marker is detected to have moved outside the selected tolerated range of movement.

16. The workflow management safety method according to claim 10 further comprising the step of reporting the position of the patient optical marker.

17. A computer-readable carrier medium carrying computer readable instructions that when executed by a data processing apparatus cause the data processing apparatus to:
  detect a patient unique identifier from a patient radiofrequency identification (RFID) tag;
  monitor a plurality of optical markers, wherein in at least one patient optical marker is positioned on the patient and at least one reference optical marker is positioned at a reference point on the radiotherapy equipment;
  monitor at least one accessory optical marker positioned on or within a radiotherapy equipment accessory; and
  match the patient unique identifier to the patient treatment plan and to the at least one accessory optical marker.

\* \* \* \* \*